(12) United States Patent
Wang et al.

(10) Patent No.: US 8,293,907 B2
(45) Date of Patent: Oct. 23, 2012

(54) PREPARATION OF SATURATED KETONE MORPHINAN COMPOUNDS BY CATALYTIC ISOMERIZATION

(75) Inventors: Peter X. Wang, Creve Coeur, MO (US); Tao Jiang, Chesterfield, MO (US); David W. Berberich, St. Peters, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 245 days.

(21) Appl. No.: 12/757,064

(22) Filed: Apr. 9, 2010

(65) Prior Publication Data
US 2010/0261904 A1 Oct. 14, 2010

Related U.S. Application Data

(60) Provisional application No. 61/167,876, filed on Apr. 9, 2009.

(51) Int. Cl.
*C07D 221/28* (2006.01)
(52) U.S. Cl. ........................................................ 546/74
(58) Field of Classification Search .................. 546/74
See application file for complete search history.

(56) References Cited

U.S. PATENT DOCUMENTS

| | | | |
|---|---|---|---|
| 2,544,291 A | 3/1951 | Baizer | |
| 2,577,947 A | 12/1951 | Baizer et al. | |
| 2,628,962 A | 2/1953 | Homeyer et al. | |
| 2,649,454 A | 2/1953 | Rapoport | |
| 2,654,756 A | 10/1953 | Homeyer et al. | |
| 2,715,626 A | 8/1955 | Pfister, III | |
| 5,571,685 A | 11/1996 | Hailes et al. | |
| 5,847,142 A | 12/1998 | Mudryk et al. | |
| 6,589,960 B2 | 7/2003 | Harclerode et al. | |
| 7,321,038 B2 | 1/2008 | Wang et al. | |
| 7,323,565 B2 | 1/2008 | Wang et al. | |
| 7,399,038 B2 | 7/2008 | Vandewinckel et al. | |
| 7,399,859 B1 | 7/2008 | Kouznetsov | |
| 2006/0155130 A1 | 7/2006 | Wang | |

OTHER PUBLICATIONS

Cadierno et. al. "Bis(allyl)-Ruthenium(IV) Complexes: Promising Precursors for Catalytic Organic Synthesis" Current Organic Chemistry 2006, 10, 165-183.*
Chmely et. al. "Complexes with Sterically Bulky Allyl Ligands: Insights into Structure and Bonding" Eur. J. Inorg. Chem. 2010, 1321-1337.*
Sivaramakrishna "Hydrocarbon (___ and _ ) complexes of nickel, palladium and platinum: Synthesis, reactivity and applications" Coordination Chemistry Reviews 254 (2010) 2904-2932.*
Standfuss "Allyl complexes of scandium: synthesis and structure of neutral, cationic and anionic derivatives" Chem. Commun., 2011, 47, 11441-11443.*
Rapoport et al., "The Preparation of Some Dihydro Ketones in the Morphine Series by Oppenauer Oxidation", J.Org. Chem., 15, 1950, pp. 1103-1107.
Baizer et al., "The Rearrangement of codeing to Dihydrocodeinone", J. Am. Pharm. Assoc., 40, 1950, pp. 580-582.
Rimland et al., "Synthesis of *N*-[Methyl-$^{11}$C]Hydromorphone by Using Multivariate Strategies for Optimization of Radiochemical Yields", Appl. Radiat. Isot., 38, 1987, p. 651.
Cadierno et al., "Bis(allyl)-ruthenium(IV) complexes as highly efficient catalysts for the redox . . . ", Journal of the American Chemical Society, 128, 2006, pp. 1360-1370, XP 002586561.

* cited by examiner

*Primary Examiner* — David K O'Dell

(57) ABSTRACT

The present invention provides processes for the preparation of saturated ketone morphinan compounds by catalytic isomerization. In particular, the invention provides processes for the conversion of a morphinan comprising an allyl alcohol ring moiety into a morphinan comprising a saturated ketone ring moiety by an isomerization reaction catalyzed by an allyl-transition metal catalyst.

19 Claims, No Drawings

PREPARATION OF SATURATED KETONE MORPHINAN COMPOUNDS BY CATALYTIC ISOMERIZATION

CROSS REFERENCE TO RELATED APPLICATIONS

This application claims the benefit of U.S. Provisional Application No. 61/167,876 filed Apr. 9, 2009, which is incorporated herein in its entirety.

FIELD OF THE INVENTION

The present invention generally relates to the preparation of saturated ketone morphinan compounds by catalytic isomerization. In particular, the invention relate to the use of allyl-transition metal catalyst to convert a morphinan comprising an allyl alcohol ring moiety into a morphinan comprising a saturated ketone ring moiety.

BACKGROUND OF THE INVENTION

Hydromorphone and hydrocodone are opioid analgesic drugs available in the market and both are generally used for relief of moderate to severe pain in patients where an opioid analgesic is appropriate. Hydrocodone is the most frequently prescribed opiate in the United States. Although hydromorphone is two to three times more potent than hydrocodone, it is also at least two to four times more expensive than hydrocodone. The higher cost of hydromorphone is due to the difficulty of its production. Despite this, however, prescriptions for hydromorphone products increased from about 0.47 million in 1998 to about 1.83 million in 2006. The aggregate production quota for hydromorphone as established by DEA increased from 766 kilograms in 1998 to 3,300 kilograms in 2006.

One of the current methods for the production of hydromorphone or hydrocodone involves a two-step oxidation/reduction route from morphine or codeine, respectively. This method, however, is expensive and inefficient. The reaction is carried out in the presence of a strong base such as potassium tert-butoxide, and under this severe reaction condition, dimers are formed as impurities that are very difficult to remove. Another production method utilizes isomerization of morphine to hydromorphone in the presence of a late transition metal and metal chloride. The method was originally developed in Germany a half century ago and modified a decade ago. Theoretically, the catalyst is formed in situ under a severe reaction condition in which the conversion between metal and metal ion occurs. Even though the isomerization of morphine to hydromorphone proceeds well, the side reactions of catalytic dimerizations and formation of dihydromorphine by reducing morphine or hydromorphone are also significant. Each of the current production methods generates only a moderate yield in an industrial environment, typically 40%-60% mole/mole even after optimization, due to the difficulty in the removal of impurities. Thus, there is a need for new processes for producing hydromorphone at lower costs, with higher yield and higher purity to meet the increasing demand for hydromorphone.

SUMMARY OF THE INVENTION

Among the various aspects of the present invention is the provision of processes for the preparation of saturated ketone morphinans by one-step isomerization reactions catalyzed by allyl-transition metal catalysts.

One aspect of the invention encompasses a process for the preparation of a morphinan comprising a saturated ketone ring moiety. The process comprises contacting a morphinan comprising an allyl alcohol ring moiety with an allyl-transition metal catalyst under acidic conditions such that the allyl alcohol ring moiety is catalytically isomerized to the saturated ketone ring moiety.

Another aspect of the invention provides a process for the preparation of a compound comprising Formula (II). The process comprises contacting a compound comprising Formula (I) with an allyl-transition metal catalyst and a proton donor to form the compound comprising Formula (II):

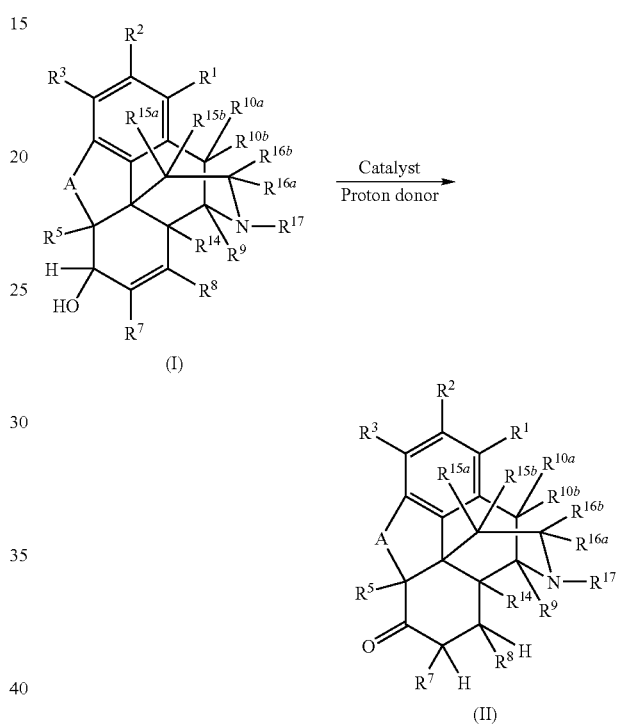

wherein:

A is a heteroatom selected the group consisting of oxygen and sulfur;

$R^1$, $R^2$, and $R^3$ are independently selected from the group consisting of hydrogen, halogen, hydroxy, protected hydroxy, {—}SH, {—}SR$^{1611}$, {—}OR$^{1611}$, and {—}NR$^{1611}$R$^{1612}$, hydrocarbyl, and substituted hydrocarbyl;

$R^5$, $R^7$, $R^8$, $R^9$, $R^{10a}$, $R^{10b}$, $R^{14}$, $R^{15a}$, $R^{15b}$, $R^{16a}$, $R^{16b}$, and $R^{17}$ are independently selected from the group consisting of hydrogen, halogen, hydroxy, {—}SH, {—}SR$^{1611}$, {—}OR$^{1611}$, and {—}NR$^{1611}$R$^{1612}$, hydrocarbyl, and substituted hydrocarbyl; provided that any of $R^{10a}$ and $R^{10b}$, $R^{15a}$ and $R^{15b}$, and $R^{16a}$ and $R^{16b}$ may together form a moiety selected from the group consisting of {=}O, {=}S, and {=}NR$^{1613}$;

$R^{1611}$, $R^{1612}$, and $R^{1613}$ are independently selected from the group consisting of hydrocarbyl, and substituted hydrocarbyl; and one or more of $R^1$, $R^2$, $R^3$, $R^5$, $R^7$, $R^8$, $R^9$, $R^{10a}$, $R^{10b}$, $R^{14}$, $R^{15a}$, $R^{15b}$, $R^{16a}$, and $R^{16b}$ may form part of a ring or ring system selected from the group consisting of carbocyclic, heterocyclic, aryl, heteroaryl, and combinations thereof.

Another aspect of the present invention provides a process for the preparation of a compound comprising Formula (IIa). The process comprises contacting a compound comprising Formula (Ia) with an allyl-transition metal catalyst to form the compound comprising Formula (IIa):

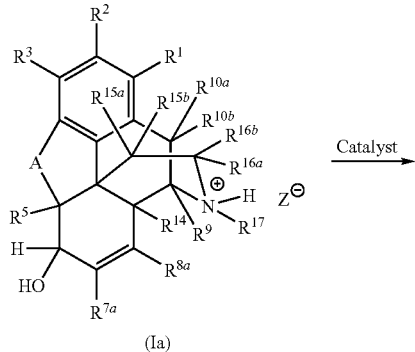

(Ia)

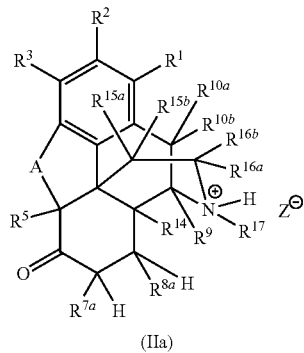

(IIa)

wherein:
A is a heteroatom selected the group consisting of oxygen and sulfur;
$R^1$, $R^2$, and $R^3$ are independently selected from the group consisting of hydrogen, halogen, hydroxy, protected hydroxy, {—}SH, {—}SR$^{1611}$, {—}OR$^{1611}$, and {—}NR$^{1611}$R$^{1612}$, hydrocarbyl, and substituted hydrocarbyl;
$R^5$, $R^7$, $R^8$, $R^9$, $R^{10a}$, $R^{10b}$, $R^{14}$, $R^{15a}$, $R^{15b}$, $R^{16a}$, $R^{16b}$, and $R^{17}$ are independently selected from the group consisting of hydrogen, halogen, hydroxy, {—}SH, {—}SR$^{1611}$, {—}OR$^{1611}$, and {—}NR$^{1611}$R$^{1612}$, hydrocarbyl, and substituted hydrocarbyl; provided that any of $R^{10a}$ and $R^{10b}$, $R^{15a}$ and $R^{15b}$, and $R^{16a}$ and $R^{16b}$ may together form a moiety selected from the group consisting of {═}O, {'}S, and {═}NR$^{1613}$;
$R^{1611}$, $R^{1612}$, and $R^{1613}$ are independently selected from the group consisting of hydrocarbyl, and substituted hydrocarbyl;
one or more of $R^1$, $R^2$, $R^3$, $R^5$, $R^7$, $R^8$, $R^9$, $R^{10a}$, $R^{10b}$, $R^{14}$, $R^{15a}$, $R^{15b}$, $R^{16a}$, and $R^{16b}$ may form part of a ring or ring system selected from the group consisting of carbocyclic, heterocyclic, aryl, heteroaryl, and combinations thereof; and
Z is a pharmaceutically acceptable salt.
Other aspects and features of the invention are detailed below.

DETAILED DESCRIPTION OF THE INVENTION

The present invention provides efficient processes for the preparation of saturated ketone morphinans by catalytic isomerization. More specifically, the processes utilize an allyl-transition metal complex to catalyze isomerization of a morphinan comprising an allyl alcohol ring moiety into morphinan comprising a saturated ketone ring moiety. In exemplary embodiments, morphine or codeine is catalytically isomerized into hydromorphone or hydrocodone, respectively. The processes of the invention comprise a one-pot process that proceeds under acidic conditions. These catalytic isomerization reactions are not only efficient, but also have increased yields with fewer impurities than previous methods.

Processes for the Preparation of Morphinans Comprising Saturated Ketone Ring Moieties One aspect of the present invention encompasses a process for the preparation of a saturated ketone morphinan compound comprising Formula (II). The process comprises contacting an allyl alcohol morphinan compound comprising Formula (I) with an allyl-transition metal catalyst and a proton donor, wherein the compound comprising Formula (I) undergoes a double bond isomerization to form the compound comprising Formula (II). For the purposes of illustration, Reaction Scheme 1 depicts preparation of the compound comprising Formula (II) according to this aspect of the invention:

Reaction Scheme 1

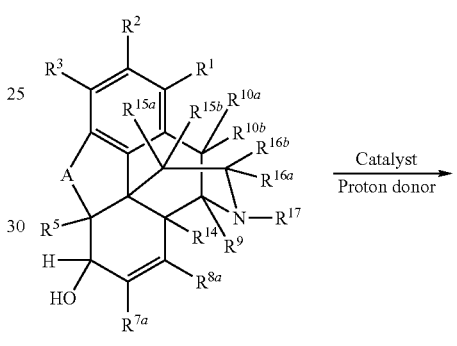

(I)

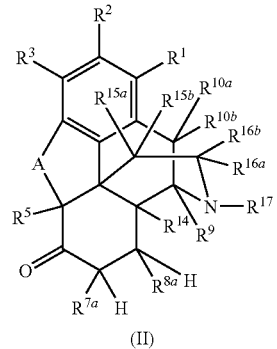

(II)

wherein:
A is a heteroatom selected the group consisting of oxygen and sulfur;
$R^1$, $R^2$, and $R^3$ are independently selected from the group consisting of hydrogen, halogen, hydroxy, protected hydroxy, {—}SH, {—}SR$^{1611}$, {—}OR$^{1611}$, and {—}NR$^{1611}$R$^{1612}$, hydrocarbyl, and substituted hydrocarbyl;
$R^5$, $R^7$, $R^8$, $R^9$, $R^{10a}$, $R^{10b}$, $R^{14}$, $R^{15a}$, $R^{15b}$, $R^{16a}$, $R^{16b}$, and $R^{17}$ are independently selected from the group consisting of hydrogen, halogen, hydroxy, {—}SH, {—}SR$^{1611}$, {—}OR$^{1611}$, and {—}NR$^{1611}$R$^{1612}$, hydrocarbyl, and substituted hydrocarbyl; provided that any of $R^{10a}$ and $R^{10b}$, $R^{15a}$ and $R^{15b}$, and $R^{16a}$ and $R^{16b}$ may together form a moiety selected from the group consisting of {═}O, {═}S, and {═}NR$^{1613}$;
$R^{1611}$, $R^{1612}$, and $R^{1613}$ are independently selected from the group consisting of hydrocarbyl, and substituted hydrocarbyl; and one or more of $R^1$, $R^2$, $R^3$, $R^5$, $R^7$, $R^8$, $R^9$, $R^{10a}$, $R^{10b}$, $R^{14}$, $R^{15a}$, $R^{15b}$, $R^{16a}$, and $R^{16b}$ may form part of a ring or ring system selected from the group consisting of carbocyclic, heterocyclic, aryl, heteroaryl, and combinations thereof.

In a preferred embodiment, A is oxygen. In another preferred embodiment, each of $R^1$, $R^2$, $R^5$, $R^7$, $R^8$, $R^9$, $R^{10a}$, $R^{10b}$, $R^{15a}$, $R^{15b}$, $R^{16a}$, and $R^{16b}$ is hydrogen. In still another preferred embodiment, $R^3$ is selected from the group consisting of hydroxy, protected hydroxy, alkyloxy, and acyloxy. In yet another preferred embodiment, $R^{17}$ is selected from the group consisting of hydrogen, alkyl, cycloalkyl, cycloalkylmethyl, allyl, and aryl. In a further preferred embodiment, $R^{14}$ is hydrogen or hydroxy.

In one exemplary embodiment, A is oxygen; each of $R^1$, $R^2$, $R^5$, $R^7$, $R^5$, $R^9$, $R^{10a}$, $R^{10b}$, $R^{15a}$, $R^{15b}$, $R^{16a}$, and $R^{16b}$ is hydrogen; $R^3$ is hydroxy; $R^{14}$ is hydrogen; and $R^{17}$ is methyl. In another exemplary embodiment, A is oxygen; each of $R^1$, $R^2$, $R^5$, $R^7$, $R^5$, $R^9$, $R^{10a}$, $R^{10b}$, $R^{15a}$, $R^{15b}$, $R^{16a}$, and $R^{16b}$ is hydrogen; $R^3$ is methoxy; $R^{14}$ is hydrogen; and $R^{17}$ is methyl.

Another aspect of the invention provides a process for the preparation of a compound comprising Formula (IIa), which is a pharmaceutically acceptable salt of the compound comprising Formula (II). The process comprises contacting a compound comprising Formula (Ia), which is a pharmaceutically acceptable salt of the compound comprising Formula (I), with an allyl-transition metal catalyst, wherein the compound comprising Formula (Ia) undergoes a double bond isomerization to form the compound comprising Formula (IIa). For the purposes of illustration, Reaction Scheme 2 depicts the preparation of the compound comprising Formula (IIa), according to this aspect of the invention:

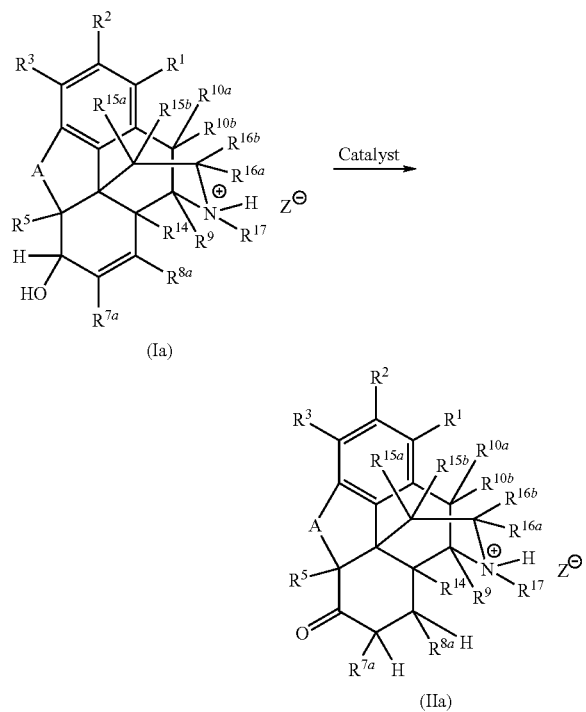

wherein:
$R^2$, $R^3$, $R^5$, $R^7$, $R^8$, $R^9$, $R^{10a}$, $R^{10b}$, $R^{14}$, $R^{15a}$, $R^{15b}$, $R^{16a}$, $R^{16b}$, and $R^{17}$ are as defined above for the compounds comprising Formulas (I) and (II); and
Z is a pharmaceutically acceptable salt.

In a preferred embodiment, A is oxygen. In another preferred embodiment, each of $R^1$, $R^2$, $R^5$, $R^7$, $R^8$, $R^9$, $R^{10a}$, $R^{10b}$, $R^{15a}$, $R^{15b}$, $R^{16a}$, and $R^{16b}$ is hydrogen. In still another preferred embodiment, $R^3$ is selected from the group consisting of hydroxy, protected hydroxy, alkyloxy, and acyloxy. In yet another preferred embodiment, $R^{17}$ is selected from the group consisting of hydrogen, alkyl, cycloalkyl, cycloalkylmethyl, allyl, and aryl. In a further preferred embodiment, $R^{14}$ is hydrogen or hydroxy.

In preferred embodiments, Z is selected from the group consisting of acetate, aspartate, benzoate, bitartrate, citrate, formate, gluconate, glucuronate, glutamate, fumarate, hydrochloride, hydrobromide, hydroiodide, hypophosphite, isobutyrate, isocitrate, lactate, malate, maleate, meconate, methanesulfonate, monohydrate, mucate, nitrate, oxalate, phenylpropionate, phosphate, phthalate, propionate, pyruvate, salicylate, stearate, succinate, sulfate, tannate, tartrate, terephthalate, valerate, and the like. In exemplary embodiments, Z is sulfate, hydrochloride, or bitartrate.

In one exemplary embodiment, A is oxygen; each of $R^1$, $R^2$, $R^5$, $R^7$, $R^8$, $R^9$, $R^{10a}$, $R^{10b}$, $R^{15a}$, $R^{15b}$, $R^{16a}$, and $R^{16b}$ is hydrogen; $R^3$ is hydroxy; $R^{14}$ is hydrogen; $R^{17}$ is methyl; and Z is sulfate or hydrochloride. In another exemplary embodiment, A is oxygen; each of $R^1$, $R^2$, $R^5$, $R^7$, $R^6$, $R^9$, $R^{10a}$, $R^{10b}$, $R^{15a}$, $R^{15b}$, $R^{16a}$, and $R^{16b}$ is hydrogen; $R^3$ is methoxy; $R^{14}$ is hydrogen; $R^{17}$ is methyl; and Z is sulfate, hydrochloride, or bitartrate.

(a) Reaction Mixture

The processes of the invention comprise one-pot processes in which the compound comprising Formulas (I) or (Ia) is contacted with an allyl-transition metal catalyst under acidic conditions such that the allyl alcohol ring moiety of the compound comprising Formulas (I) or (Ia) is catalytically isomerized to the saturated ketone ring moiety of the compound comprising Formulas (II) or (IIa), respectively.

(i) Allyl-Transition Metal Catalyst

The reaction mixture comprises the substrate, i.e., the compound comprising Formulas (I) or (Ia), and the allyl-transition metal catalyst. In preferred embodiments, the transition metal of the allyl-transition metal catalyst may be ruthenium, osmium, rhodium, iridium, nickel, palladium, or platinum. The valence state of the transition metal may vary. For example, non-limiting examples of suitable transition metals include ruthenium(II), ruthenium(III), ruthenium(IV), osmium(II), osmium(III), osmium(IV), rhodium(I), rhodium (III), iridium(III), iridium(IV), nickel(II), palladium(II), palladium(IV), platinum(II), and platinum(IV). In an exemplary embodiment, the transition metal catalyst of the allyl-transition metal catalyst may be ruthenium. The ruthenium may be ruthenium(II) or ruthenium(IV). In preferred embodiments, the ally-transition metal catalyst may comprise a bis(allyl-ruthenium) complex. In exemplary embodiments, the bis(allylkruthenium) complex may be a bis-$\eta^3$-bonded ruthenium complex.

In one embodiment, the bis-$\eta^3$-bonded ruthenium complex may comprise Formula (III):

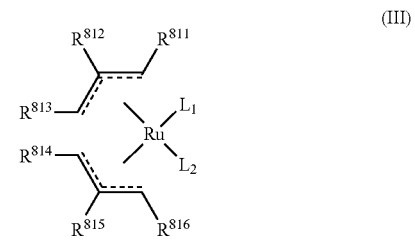

wherein:
$R^{811}$, $R^{812}$, $R^{813}$, $R^{814}$, $R^{815}$, and $R^{816}$ are independently selected from the group consisting of hydrocarbyl and substituted hydrocarbyl; provided one or more of $R^{811}$, $R^{812}$, $R^{813}$, $R^{814}$, $R^{815}$, and $R^{816}$ may form part of a ring or ring system selected from the group consisting of carbocyclic, heterocyclic, aryl, heteroaryl, and combinations thereof; provided two or more of $R^{811}$, $R^{813}$, $R^{814}$, and $R^{816}$ may link together to form a longer chain; and $L_1$ and $L_2$ are independently selected from the group consisting of anion, hydrocarbyl, and substituted hydrocarbyl; provided $L_1$ and $L_2$ together may form the anion, a hydrocarbyl moiety, or a substituted hydrocarbyl moiety.

In another embodiment, the bis-$\eta^3$-bonded ruthenium complex may comprise Formula (IV):

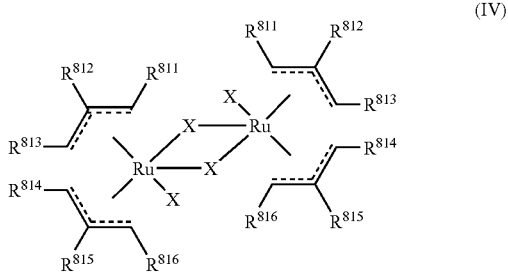

(IV)

wherein:
$R^{811}$, $R^{812}$, $R^{813}$, $R^{814}$, $R^{815}$, and $R^{816}$ are as defined above for the compound comprising Formula (III); and
X is halogen selected from the group consisting of chloride, bromide, and iodide.

In yet another embodiment, the bis-$\eta^3$-bonded ruthenium complex may comprise Formula (V):

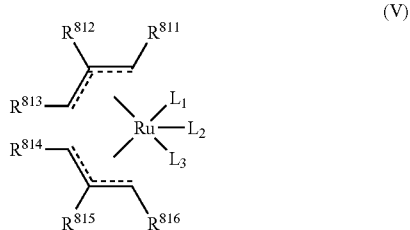

(V)

wherein:
$R^{811}$, $R^{812}$, $R^{813}$, $R^{814}$, $R^{815}$, $R^{616}$, $L_1$, and $L_2$ are as defined above for the compound comprising Formula (III); and
$L_1$ and $L_2$ are independently selected from the group consisting of anion, hydrocarbyl, and substituted hydrocarbyl; provided $L_1$ and $L_2$ together may form the anion, a hydrocarbyl moiety, or a substituted hydrocarbyl moiety; and
$L_3$ is a coordinated ligand.

In preferred embodiments, $L_1$ and $L_2$ of the compounds comprising Formulas (III) or (V) are anions. The anions may be the same or different. Non-limiting examples of suitable anions include hydride, halogen (e.g., chloride, bromide, or iodide), $MeSO_{3-}$, p-$MeC_6H_4SO_{3-}$, $H_2PO_{4-}$, $CF_3SO_{3-}$, $ClO_{4-}$, $PF_{6-}$, $BF_{4-}$, $CF_3SO_{3-}$, $HSO_{4-}$, hydrocarbyl anion, and substituted hydrocarbyl anion. In one embodiment, $L_1$ and $L_2$ together may form an anion with a −2 charge, such as $SO_4^{2-}$ or $HPO_4^{2-}$. The hydrocarbyl or substituted hydrocarbyl anion may be $RO^-$, $RCO_{2-}$, and $RSO_{3-}$, wherein R is hydrocarbyl or substituted hydrocarbyl. Preferably, R may be methyl, ethyl, propyl, isopropyl, butyl, isobutyl, t-butyl, phenyl, or substituted versions thereof.

In other preferred embodiments, $L_3$ of the compound comprising Formula (V) is a coordinated ligand or solvent selected from the group consisting of water, alcohol, acetonitrile, acetone, carbon monoxide, ether, N,N-dimethylformamide, dimethyl sulfoxide, N-methylpyrrolidone, propylamine, pyridine, triphenylphosphine, and tetrahydrofuran. In other preferred embodiments, the amine functional group of the compound comprising Formulas (I) or (Ia) may be coordinated to the transition metal of the catalyst. Stated another way, the amine functional group of the morphinan substrate may function as $L_3$.

The valence state of the ruthenium ion of the compound comprising Formulas (III), (IV), or (V) may vary. The ruthenium ion may have a charge of +4, i.e., ruthenium(IV), or a charge of +2, i.e., ruthenium(II). The lower valence state may be made by reduction of ruthenium(IV) or by adding two protons to any of the compounds comprising Formulas (III), (IV), or (V), as depicted above. Reduction may be accomplished by contact with hydrogen or a reducing agent. Non-limiting examples of suitable reducing agents include hydrides (e.g., sodium hydride, lithium hydride, and potassium hydride, lithium aluminum hydride, sodium borohydride, sodium cyanoborohydride, and the like), or combinations of a metal (e.g., tin, zinc, or iron) or a metal compound (e.g., chromium chloride, chromium acetate, and the like) with an organic or inorganic acid (e.g., formic acid, hydrophosphorous acid, and the like), samarium iodide, and others. The lower valence state of the compound comprising Formulas (III), (IV), or (V) may be inherent to the compound or may be made in situ.

In exemplary embodiments, the bis-$\Theta^3$-bonded ruthenium complex may be $\{Ru(\Theta^3:\Theta^3-C_{10}H_{16})(\mu-Cl)Cl\}_2$, which is a dimer of $\Theta^3:\Theta^3$-2,7-dimethyl-2,6-octadiene-1,8-diyl-ruthenium(IV) dichloride; $Ru(\Theta^3:\Theta^2:\Theta^3-C_{12}H_{18})Cl_2$, which is $\Theta^3:\Theta^2:\Theta^3$-dodeca-2,6,10-triene-1,12,diyl-ruthenium(IV) dichloride; $\{Ru(\Theta^3:\Theta^3-C_{12}H_{20})(\mu-Cl)Cl\}_2$, which is a dimer of $\Theta^3:\Theta^3$-2,3,6,7-tetramethyl-2,6-octadiene-1,8-didyl-ruthenium(IV) dichloride; or bis($\Theta^3$-allyl)-ruthenium-(1,5-cyclooactadiene). In an exemplary embodiment, the bis-$\Theta^3$-bonded ruthenium complex may be $\{Ru(\Theta^3:\Theta^3-C_{10}H_{16})(\mu-Cl)Cl\}_2$.

The weight:weight ratio of the compound comprising Formulas (I) or (Ia) to the allyl-transition metal catalyst can and will vary. In general, the weight:weight ratio of the compound comprising Formulas (I) or (Ia) to the allyl-transition metal catalyst may range from about 1:0.0001 to about 1:0.05. in various embodiments, the weight:weight ratio of the compound comprising Formulas (I) or (Ia) to the allyl-transition metal catalyst may range from about 1:0.0001 to about 1:0.001, from about 1:0.001 to about 1:0.01, or from about 1:0.01 to about 1:0.05. In preferred embodiments, the weight:weight ratio of the compound comprising Formulas (I) or (Ia) to the allyl-transition metal catalyst may range from about 1:0.002 to about 1:0.04. In an exemplary embodiment, the weight:weight ratio of the compound comprising Formulas (I) or (Ia) to the allyl-transition metal catalyst may range form about 1:0.005 to about 1:0.02, or more preferably about 1:0.01.

(ii) Optional Proton Donor

The processes of the invention comprise contacting the substrate, i.e., the compound comprising Formulas (I) or (Ia), with the allyl-transition metal catalyst under acidic conditions. In embodiments in which the substrate is the free base, i.e., the compound comprising Formula (I), the process further comprises contacting the substrate and the catalyst with a proton donor. In embodiments in which the substrate is a pharmaceutically acceptable salt, i.e., the compound comprising Formula (Ia), the process may further comprise contacting the substrate and the catalyst with an optional proton donor.

A variety of proton donors are suitable for use in the processes of the invention. In general, the proton donor has a pKa of less than about 5, and preferably less than about 0, Suitable proton donors include, without limit, HOAc, $HCO_2H$, $H_2CO_3$, $MeSO_3H$, poly $H_3PO_4$, $H_3PO_4$, $H_2SO_4$, HCl, HBr, $HClO_4$, HI, $HNO_3$, $CF_3SO_3H$, p-methyltoluenesulfonic acid, $HClO_3$, $HBrO_4$, $HIO_3$, $HIO_4$, and combinations thereof. In an exemplary embodiment, the proton donor may be methanesulfonic acid ($MeSO_3H$). In another exemplary embodiment, the proton donor may be hydrochloric acid (HCl).

The amount of proton donor that is contacted with the compound comprising Formula (I) can and will vary, depending upon several factors including the identity of the proton donor. In general, sufficient proton donor is contacted with the substrate to create a reaction mixture having a pH level that ranges from about 0 to about 7. In preferred embodiments, the pH of the reaction mixture may range from 1 to about 5. The mole:mole ratio of the compound comprising Formula (I) to the proton donor may range from about 1:0.1 to about 1:5. In some embodiments, the mole:mole ratio of the compound comprising Formula (I) to the proton donor may be about 1:0.1, about 1:0.2, about 1:0.5, about 1:1, about 1:1.5, about 1:2, about 1:2.5, about 1:3, about 1:3.5, about 1:4, about 1:4.5, or about 1:5. In an exemplary embodiment, the mole:mole ratio of the compound comprising Formula (I) to the proton donor may be about 1:1.5.

In embodiments in which the substrate is the compound comprising Formula (Ia), the substrate comprises a proton source. That is, the mole:mole ratio of the compound comprising Formula (Ia) to the proton source is 1:1. In general, upon dissolution of the compound comprising Formula (Ia) in a solution, the solution typically has a pH that ranges from about 3 to about 7. In some of these embodiments, however, additional proton donor may be added to the reaction mixture. Suitable proton donors and addition rates are detailed above. In general, additional proton donor may enhance both the rate and the turnover number of the catalytic reaction.

(iii) Solvent

In general, the processes of the invention are performed in the presence of a solvent. The solvent may be a protic solvent, an aprotic solvent, or combinations thereof. Non-limiting examples of suitable protic solvents include methanol, ethanol, isopropanol, n-propanol, isobutanol, n-butanol, s-butanol, t-butanol, formic acid, acetic acid, water, and combinations thereof. Examples of suitable aprotic solvents include, but are not limited to, acetone, acetonitrile, diethoxymethane, N,N-dimethylformamide (DMF), N,N-dimethylpropionamide, 1,3-dimethyl-3,4,5,6-tetrahydro-2 (1H-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), 1,4-dioxane, N-methyl-2-pyrrolidinone (NMP), ethyl acetate, ethyl formate, ethyl methyl ketone, formamide, hexachloroacetone, hexamethylphosphoramide, methyl acetate, N-methylacetamide, N-methylformamide, methylene chloride, nitrobenzene, nitromethane, propionitrile, sulfolane, tetramethylurea, tetrahydrofuran (THF), 2-methyl tetrahydrofuran, trichloromethane, and combinations thereof. In preferred embodiments, the solvent may be a protic solvent. In one preferred embodiment, the solvent may be an alcohol. In another preferred embodiment, the solvent may be ethanol. In still another preferred embodiment, the solvent may be a mixture of ethanol and water.

The weight:weight ratio of the solvent to the compound comprising Formulas (I) or (Ia) can and will vary. Typically, the weight:weight ratio of the solvent to the compound comprising Formulas (I) or (Ia) may range from about 0.5:1 to about 10:1. In various embodiments, the weight:weight ratio of the solvent to the compound comprising Formulas (I) or (Ia) may range from about 0.5:1 to about 2:1, from about 2:1 to about 5:1, from about 5:1 to about 10:1. In preferred embodiments, the weight:weight ratio of the solvent to the compound comprising Formulas (I) or (Ia) may range from about 2:1 to about 4:1.

(b) Reaction Conditions

The processes of the invention are typically performed in one step; that is, the substrate, the catalyst, the optional proton donor, and the solvent are mixed together in a reaction vessel. The reaction is allowed to proceed at a temperature that may range from about 10° to about 120° C. In preferred embodiments, the temperature of the reaction may range from about 45° to about 100° C., or more preferably from about 65° to about 100° C. In an exemplary embodiment, the temperature of the reaction may range from about 75° to about 80° C. In another exemplary embodiment, the temperature of the reaction may range from about 80° to about 100° C.

Typically, the reaction is allowed to proceed for a sufficient period of time until the reaction is complete, as determined by any method known to one skilled in the art, such as chromatography (e.g., HPLC). In this context, a "completed reaction" generally means that the reaction mixture contains a significantly diminished amount of the compound comprising Formulas (I) or (Ia) and a significantly increased amount of the compound comprising Formulas (II) or (IIa) compared to the amounts of each present at the beginning of the reaction. Typically, the amount of the compound comprising Formulas (I) or (Ia) remaining in the reaction mixture may be less than about 3%, less than about 1%, and preferably less than about 0.5%.

Upon completion of the reaction, the reaction mixture may be cooled and the product may be isolated by distillation, phase extraction, precipitation, filtration, crystallization, or other means familiar to those of skill in the art. The final product may be washed and dried, and analyzed by HPLC, UPLC, MS, NMR, IR, or TGA.

The yield of the compound comprising Formulas (II) or (IIa) can and will vary. Typically, the mole:mole yield of the compound comprising Formulas (II) or (IIa) may be at least about 60%. In preferred embodiments of the invention, the mole:mole yield of the compound comprising Formulas (II) or (IIa) may be at least about 65%, or at least about 70%. In exemplary embodiment, the mole:mole yield of the compound comprising Formulas (II) or (IIa) may be at least about 75%, at least about 80%, or at least about 85%. In another exemplary embodiment, the mole:mole yield of the compound comprising Formulas (II) or (IIa) may be at least about 90%, at least about 95%, at least 97%, or at least about 99%.

The compound comprising Formulas (II) or (IIa) prepared by the processes of the invention may be an end product itself, or may be further derivatized in one or more steps to yield further intermediates or end products. Furthermore, the compound comprising Formulas (II) may be converted into a pharmaceutically acceptable salt using techniques well known to those of skill in the art (see Examples 2 and 4). Similarly, the compound comprising Formula (IIa) may be converted into a different pharmaceutically acceptable salt using techniques well known to those of skill in the art.

(c) Stereochemistry

The substrates and the products of the processes of the invention are morphinan compounds. For the purposes of discussion, the ring atoms of a morphinan compound are numbered as diagrammed below. Morphinan compounds have asymmetric centers. In particular, the core morphinan

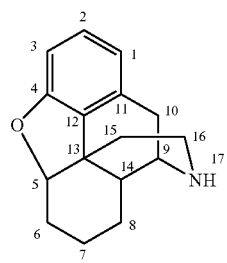

compound may have at least four chiral carbons; namely, C-5, C-13, C-14, and C-9.

Any of the compounds comprising Formulas (II) or (IIa) may have a (−) or (+) orientation with respect to the rotation of polarized light, depending upon whether the starting substrate has (−) or (+) optical activity. More specifically, each chiral center has an R or an S configuration. In particular, the configuration of the chiral carbons C-5, C-13, C-14, and C-9 may be RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face or the beta face of the molecule.

In a preferred embodiment, the compound produced by the process of the invention is a compound as diagrammed below or a pharmaceutically acceptable salt of the compound. When R is hydrogen, the compound is hydromorphone, and when R is methyl, the compound is hydrocodone. In one exemplary embodiment, the optical activity of the compound may be (+), and the configuration of C-5, C-13, C-14, and C-9, respectively, may be SRSS. In another exemplary embodiment, the optical activity of the compound may be (−), and the configuration of C-5, C-13, C-14, and C-9, respectively, may be RSRR.

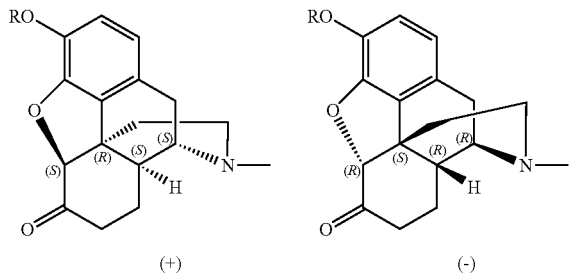

Definitions

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "allyl-transition metal catalyst," as used herein refers to coordination compounds in which a transition metal ion is complexed with at least one allyl ligand (or substituted allyl ligand) via delocalized eta ($\Theta^3$) bonds. The superscript refers to the number of electrons shared between the metal center and the allyl ligand.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen atom (and hence, forming a protected hydroxy), wherein the protecting group may be removed, subsequent to the reaction for which protection is employed, without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various embodiments of the invention.

Example 1

Catalytic Isomerization of Morphine to Hydromorphone

Morphine sulfate (11.85 g) was added to a 125 mL flask. Ethanol (36 mL), water (24 mL), and methanesulfonic acid (3.85 mL) were added. The flask was flushed with nitrogen, and the ruthenium catalyst [{Ru($\Theta^3$:$\Theta^3$-$C_{10}H_{16}$)(μ-Cl)Cl}$_2$] {180 mg, a dimer of $\Sigma^3$:$\Sigma^3$-2,7-dimethyl-2,6-octadiene-1,8-diyl-ruthenium (II) dichloride} was added. The mixture was heated at 78° C. for 5 h. HPLC analysis showed that the reaction was completed within 3 h.

The mixture was cooled to 60° C. EDTA.2Na (1.2 g) was added, and vacuum was applied slowly for distillation, Volatile solvent (36 mL) was removed. Water (12 mL) was added after the vacuum distillation. The resultant solution was slowly added to a solution of c-$NH_4OH$/water (6.0 mL/12 mL) with fast stirring to form a suspension. The pH was adjusted to 8.9 (i.e., 8.7-9.1) with c-$NH_4OH$ or HOAc. The mixture was stirred at 5-10° C. for 1 h and then filtered. The solid that was obtained was then washed with water (2×12 mL)–12.8 g of wet solid was obtained.

The wet cake was transferred to a flask, Water (30 mL), isopropanol (IPA) (10 mL), and HOAc (3 mL) were added. The pH was adjusted to 4-5 with c-$NH_4OH$ or HOAc. Charcoal (240 mg) was added to form a slurry. The slurry was heated to 35° C. and maintained at that temperature for 30 min. The slurry was filtered and the carbon cake was washed with water (10 mL). To the filtrate solution, c-$NH_4OH$ was added until the pH was about 7.0-7.5. The solution was stirred at 35° C. for 30 min to form a suspension. The pH was further adjusted to 8.9 i.e., (8.7-9.1) with c-$NH_4OH$. The mixture was stirred at 35° C. for 30 min, cooled down to 5-10° C. for 1 h, and filtered. The solid was dried at 65° C. under vacuum for 18 h to give 10.22 g of white solids, Example 2

Conversion of Hydromorphone Base to Hydromorphone.HCl

The above-synthesized hydromorphone (8.50 g) was added to a flask (125 mL). Water (6 mL) and IPA (12 mL) were added. The mixture was stirred to form a homogeneous slurry. The slurry was heated to 40-50° C. to dissolve all of the solids after c-HCl (1.85 mL) was added. Additional c-HCl (0.62 mL) and IPA (36 mL) were then added slowly to form crystals. The mixture was maintained at 40-50° C. for 30 min, cooled down to 5-10° C. over 1 h, maintained at 5-10° C. for 1 h, and filtered. The solid obtained was washed with IPA (2×8.5 mL), dried under vacuum at 65° C. for 18 h to give 8.83 g of pure hydromorphone.HCl as solids.

Example 3

Catalytic Isomerization of Codeine to Hydrocodone

Codeine (12.0 g) was charged to a 125 mL flask. Ethanol (36 mL), water (24 mL), and methanesulfonic acid (3.84 ml) were added. The flask was flushed with nitrogen, and the ruthenium catalyst [{Ru($\Theta^3$:$\Theta^3$-$C_{10}H_{16}$)($\mu$-Cl)Cl}$_2$] {180 mg, a dimer of $\Theta^3$:$\Theta^3$-2,7-dimethyl-2,6-octadiene-1,8-diyl-ruthenium (II) dichloride} was added. The mixture was heated at 78° C. for 5 h. HPLC analysis showed that the reaction was completed within 3 h.

The mixture was cooled to 60° C. Volatile solvent (30 mL) was removed by vacuum distillation. Water (18 mL) and charcoal (240 mg) were added after the distillation. The mixture was cooled to 35° C., maintained at that temperature for 30 min, and filtered. The carbon cake was washed with water (12 mL). To the filtrate solution, c-NH$_4$OH was added until pH=7.0-7.5. The solution was stirred at 35° C. for 30 min to form a suspension. The pH was further adjusted to 10.5 (10.0-11.0) with c-NH$_4$OH. The suspension was stirred at 35° C. for 30 min, cooled down to 5-10° C. for 1 h, and filtered. The solid obtained was washed with water (2×12 ml), dried at 65° C. under vacuum for 18 h to give 12.8 g of white solids.

Example 4

Conversion of Hydrocodone Base to Hydrocodone.HCl

Hydrocodone (8.50 g) was added to a flask (125 mL). Water (6 mL) and IPA (12 evaluation mL) were added. The mixture was stirred to form a homogeneous slurry. The slurry was heated to 40-50° C. to dissolve all of the solids after c-HCl (1.85 mL) was added. Additional c-HCl (0.58 mL) and IPA (36 mL) were then added slowly to form crystals. The mixture was maintained at 40-50° C. for 30 min, cooled down to 5-10° C. over 1 h, maintained at 5-10° C. for 1 h, and filtered. The solid obtained was washed with IPA (2×8.5 mL), dried under vacuum at 65° C. for 18 h to give 9.05 g of pure hydrocodone.HCl as white solids.

Example 5

Synthesis of [{Ru($\Theta^3$:$\Theta^3$-$C_{10}H_{16}$)($\mu$-Cl)Cl}$_2$]

The catalyst [{Ru($\eta^3$:$\eta^3$-$C_{10}H_{16}$)($\mu$-Cl)Cl}$_2$] was synthesized in 80-95% yield by heating RuCl$_3$.3H$_2$O, isoprene (2-methyl-1,3-butadiene), and ethanol, followed by distillation to remove the solvent. Heptane was added to the resultant solution to precipitate the product, which was recovered by filtration.

Example 6

Catalytic Isomerization of Morphine to Hydromorphone

Morphine sulfate (30.0 g containing morphine alkaloids 74% wt/wt) was added to a 125 mL flask. Water (60 mL), EtOH (90 mL), and methanesulfonic acid (18.0 mL) were added. The flask was flushed with nitrogen, and the ruthenium catalyst [{Ru($\Theta^3$:$\Theta^3$-$C_{10}H_{16}$)($\mu$-Cl)Cl}$_2$] {0.30 g, a dimer of $\Theta^3$:$\Theta^3$-2,7-dimethyl-2,6-octadiene-1,8-diyl-ruthenium (II) dichloride} was added. The mixture was heated to reflux for 5 h. HPLC analysis showed that the reaction was completed within 3 hours. The ratio of hydromorphone:morphine>99:1 and the purity of hydromorphone was 99% (area %).

The mixture was cooled to 60° C. EDTA.2Na (3.0 g) was added, and the resulting mixture was stirred at 60° C. for 1 h. IPA (2.0 mL) was added. c-NH$_4$OH (30.0 mL) was added with fast stirring to form a suspension. The pH was further adjusted to 8.9 (i.e., 8.7-9.1) with c-NH$_4$OH or HOAc. The mixture was stirred over an ice bath for 1 h and then filtered. The solid that was obtained was then washed with water (2×15 mL), dried in vacuum at 65° C. for 18 h to give hydromorphone base as a snow white solid, 15.1 g.

What is claimed is:

1. A one-pot process for the preparation of a morphinan comprising a saturated ketone ring moiety, the process comprising contacting a morphinan comprising an allyl alcohol ring moiety with a bis(allyl)-ruthenium (IV) complex catalyst under acidic conditions such that the allyl alcohol ring moiety is catalytically isomerized to the saturated ketone ring moiety.

2. The process of claim 1, wherein the reaction is conducted in the presence of a solvent, the solvent being chosen from a protic solvent, an aprotic solvent, and combinations thereof; and wherein the reaction is conducted at a temperature from about 10° to about 120° C.

3. A one-pot process for the preparation of a pharmaceutically acceptable salt of a morphinan comprising a saturated ketone ring moiety, the process comprising contacting a pharmaceutically acceptable salt of a morphinan comprising an allyl alcohol ring moiety with a bis(allyl)-ruthenium (IV) complex under acidic conditions such that the allyl alcohol ring moiety is catalytically isomerized to the saturated ketone ring moiety.

4. The process of claim 3, wherein the morphinan comprising the saturated ketone ring moiety is a compound having Formula (IIa) and the morphinan comprising an allyl alcohol ring moiety is a compound having Formula (Ia), wherein Formulas (IIa) and (Ia) correspond to the following structures:

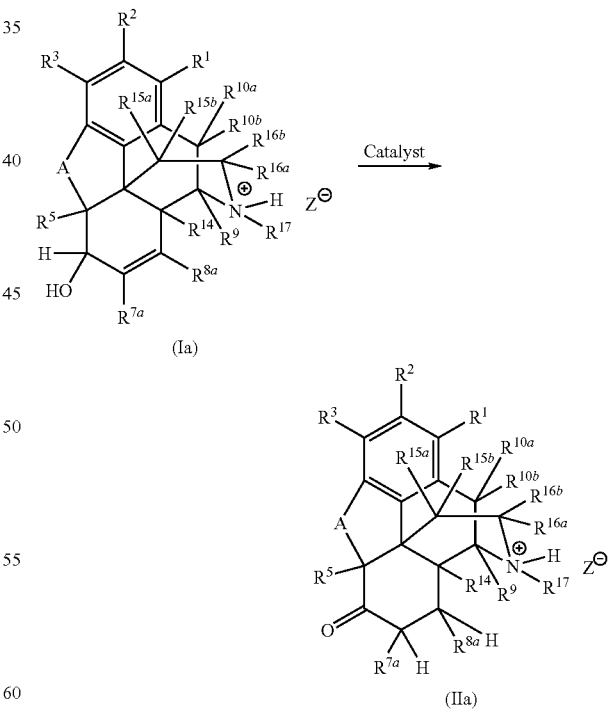

wherein:
A is a heteroatom chosen from oxygen and sulfur;
$R^1$, $R^2$, and $R^3$ are independently chosen from hydrogen, halogen, hydroxy, protected hydroxy, {—}SH, {—}SR$^{1611}$, {—}OR$^{1611}$, and {—}NR$^{1611}$R$^{1612}$, hydrocarbyl, and substituted hydrocarbyl;

$R^5$, $R^7$, $R^8$, $R^9$, $R^{10a}$, $R^{10b}$, $R^{14}$, $R^{15a}$, $R^{15b}$, $R^{16a}$, $R^{16b}$, and $R^{17}$ are independently chosen from hydrogen, halogen, hydroxy, {—}SH, {—}SR$^{1611}$, {—}OR$^{1611}$, and {—}NR$^{1611}$R$^{1612}$, hydrocarbyl, and substituted hydrocarbyl; provided that any of $R^{10a}$ and $R^{10b}$, $R^{15a}$ and $R^{15b}$, and $R^{16a}$ and $R^{16b}$ may together form a moiety chosen from {═}O, {═}S, and {═}NR$^{1613}$;

$R^{1611}$, $R^{1612}$, and $R^{1613}$ are independently chosen from hydrocarbyl, and substituted hydrocarbyl;

one or more of $R^1$, $R^2$, $R^3$, $R^5$, $R^7$, $R^8$, $R^9$, $R^{10a}$, $R^{10b}$, $R^{14}$, $R^{15a}$, $R^{15b}$, $R^{16a}$, and $R^{16b}$ may form part of a ring or ring system chosen from carbocyclic, heterocyclic, aryl, heteroaryl, and combinations thereof; and Z is a pharmaceutically acceptable salt.

5. The process of claim 4, wherein the reaction is conducted in the presence of a solvent, the solvent being chosen from a protic solvent, an aprotic solvent, and combinations thereof; and wherein the reaction is conducted at a temperature from about 10° to about 120° C.

6. A process for the preparation of a compound comprising Formula (II) or a pharmaceutically acceptable salt thereof, the process comprising contacting a compound comprising Formula (I) with a bis(ally)-ruthenium (IV) complex catalyst and a proton donor to form the compound comprising Formula (II):

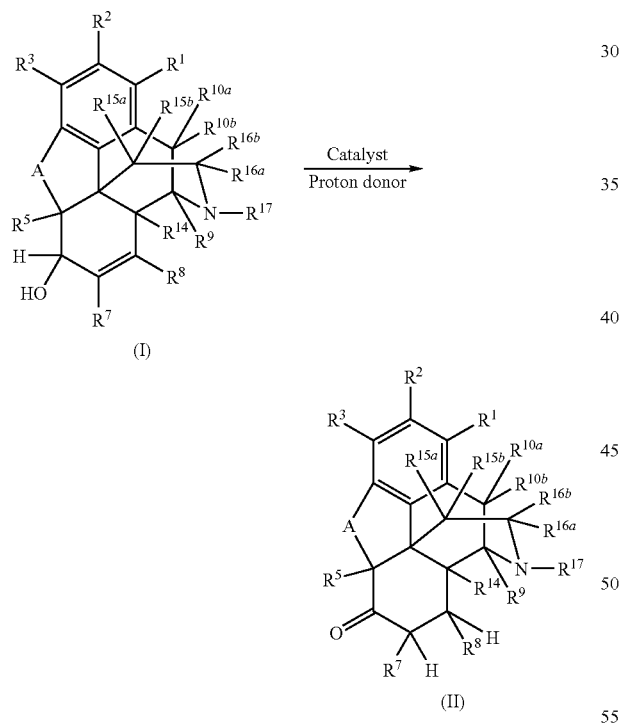

wherein:

A is a heteroatom chosen from oxygen and sulfur;

$R^1$, $R^2$, and $R^3$ are independently chosen from hydrogen, halogen, hydroxy, protected hydroxy, {—}SH, {—}SR$^{1611}$, and {—}NR$^{1611}$R$^{1612}$, hydrocarbyl, and substituted hydrocarbyl;

$R^5$, $R^7$, $R^8$, $R^9$, $R^{10a}$, $R^{10b}$, $R^{14}$, $R^{15a}$, $R^{15b}$, $R^{16a}$, $R^{16b}$, and $R^{17}$ are independently chosen from hydrogen, halogen, hydroxy, {—}SH, {—}SR$^{1611}$, {—}OR$^{1611}$, and {—}NR$^{1611}$R$^{1612}$, hydrocarbyl, and substituted hydrocarbyl; provided that any of $R^{10a}$ and $R^{10b}$, $R^{15a}$ and $R^{15b}$, and $R^{16a}$ and $R^{16b}$ may together form a moiety chosen from {═}O, {═}S, and {═}NR$^{1613}$;

$R^{1611}$, $R^{1612}$, and $R^{1613}$ are independently chosen from hydrocarbyl, and substituted hydrocarbyl; and one or more of $R^1$, $R^2$, $R^3$, $R^6$, $R^7$, $R^6$, $R^9$, $R^{10a}$, $R^{10b}$, $R^{14}$, $R^{15a}$, $R^{15b}$, $R^{16a}$, and $R^{16b}$ may form part of a ring or ring system chosen from carbocyclic, heterocyclic, aryl, heteroaryl, and combinations thereof.

7. The process of claim 6, wherein A is oxygen; $R^1$, $R^2$, $R^5$, $R^7$, $R^8$, $R^9$, $R^{10a}$, $R^{10b}$, $R^{15a}$, $R^{15b}$, $R^{16a}$, and $R^{16b}$ are hydrogen; $R^3$ is chosen from hydroxy, protected hydroxy, alkyloxy, and acyloxy; $R^{14}$ is hydrogen or hydroxy; and $R^{17}$ is chosen from hydrogen, alkyl, cycloalkyl, cycloalkylmethyl, allyl, and aryl.

8. The process of claim 7, wherein $R^3$ is hydroxy or methyoxy; $R^{14}$ is hydrogen; and $R^{17}$ is methyl.

9. The process of claim 6, wherein the catalyst is a bis-η$^3$-bonded ruthenium complex.

10. The process of claim 9, wherein the bis-η$^3$-bonded ruthenium complex is chosen from:

(a) a complex comprising Formula (III):

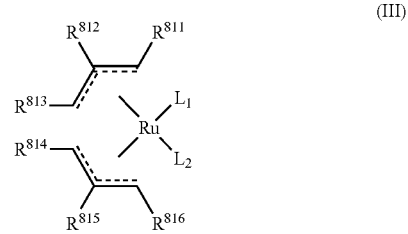

wherein:

$R^{811}$, $R^{812}$, $R^{813}$, $R^{814}$, $R^{815}$, and $R^{816}$ are independently chosen from hydrocarbyl and substituted hydrocarbyl; provided one or more of $R^{811}$, $R^{812}$, $R^{813}$, $R^{814}$, $R^{818}$, and $R^{816}$ may form part of a ring or ring system chosen from carbocyclic, heterocyclic, aryl, heteroaryl, and combinations thereof; provided two or more of $R^{811}$, $R^{813}$, $R^{814}$, and $R^{816}$ may link together to form a longer chain; and $L_1$ and $L_2$ are independently chosen from anion, hydrocarbyl, and substituted hydrocarbyl; provided $L_1$ and $L_2$ together may form the anion, a hydrocarbyl moiety, or a substituted hydrocarbyl moiety;

(b) a complex comprising Formula (IV):

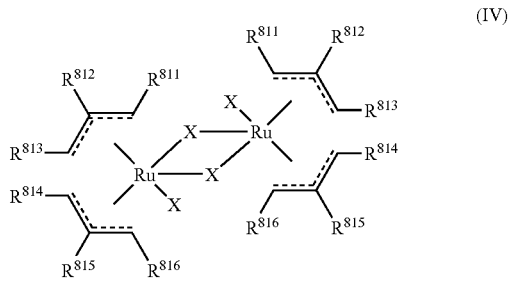

$R^{811}$, $R^{812}$, $R^{813}$, $R^{814}$, $R^{815}$, and $R^{816}$ are independently chosen from hydrocarbyl and substituted hydrocarbyl; provided one or more of $R^{811}$, $R^{812}$, $R^{813}$, $R^{814}$, $R^{815}$, and $R^{816}$ may form part of a ring or ring system chosen from carbocyclic, heterocyclic, aryl, heteroaryl, and combinations thereof; provided two or more of $R^{811}$, $R^{813}$, $R^{814}$, and $R^{816}$ may link together to form a longer chain; and X is halogen; and (c) a complex comprising Formula (V):

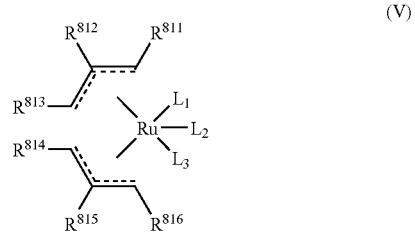

wherein:

$R^{811}$, $R^{812}$, $R^{813}$, $R^{814}$, $R^{815}$, and $R^{816}$ are independently chosen from hydrocarbyl and substituted hydrocarbyl; provided one or more of $R^{811}$, $R^{812}$, $R^{813}$, $R^{814}$, $R^{815}$, and $R^{816}$ may form part of a ring or ring system chosen from carbocyclic, heterocyclic, aryl, heteroaryl, and combinations thereof; provided two or more of $R^{811}$, $R^{813}$, $R^{814}$, and $R^{816}$ may link together to form a longer chain;

$L_1$ and $L_2$ are independently chosen from an anion, hydrocarbyl, and substituted hydrocarbyl; provided $L_1$ and $L_2$ together may form the anion, a hydrocarbyl moiety, or a substituted hydrocarbyl moiety; and $L_3$ is a coordinated ligand chosen from water, alcohol, acetonitrile, acetone, carbon monoxide, ether, N,N-dimethylformamide, N-methylpyrrolidone, propylamine, pyridine, triphenylphosphine, and tetrahydrofuran.

11. The process of claim 10, wherein the anion, if present, is chosen from hydride, halogen, $MeSO_{3-}$, $p\text{-}MeC_6H_4SO_{3-}$, $H_2PO_{4-}$, $CF_3SO_{3-}$, $ClO_{4-}$, $PF_{6-}$, $BF_{4-}$, $CF_3SO_{3-}$, $HSO_{4-}$, and hydrocarbyl or substituted hydrocarbyl anion chosen from RO—, $RCO_{2-}$, and $RSO_{3-}$, wherein R is hydrocarbyl or substituted hydrocarbyl.

12. The process of claim 6, wherein the bis(allyl)-ruthenium(IV) complex is chosen from $\{Ru(\eta^3:\eta^3\text{-}C_{10}H_{16})(\mu\text{-}Cl)Cl\}_2$, $Ru(\eta^3:\eta^2:\eta^3\text{-}C_{12}H_{18})Cl_2$, and $\{Ru(\eta^3:\eta^3\text{-}C_{12}H_{20})(\mu\text{-}Cl)Cl\}_2$.

13. The process of claim 6, wherein the proton donor has a pKa of less than 5 and is chosen from HOAc, $HCO_2H$, $H_2CO_3$, $MeSO_3H$, poly $H_3PO_4$, $H_3PO_4$, $H_2SO_4$, HCl, HBr, $HClO_4$, HI, $HNO_3$, $CF_3SO_3H$, p-methyltoluenesulfonic acid, $HClO_3$, $HBrO_4$, $HIO_3$, $HIO_4$, and combinations thereof.

14. The process of claim 6, wherein the weight:weight ratio of the compound comprising Formula (I) to the catalyst is from about 1:0.0001 to about 1:0.05, the mole:mole ratio of the compound comprising Formula (I) to the proton donor is from about 1:0.1 to about 1:5; the reaction is conducted in the presence of a solvent; the weight:weight ratio of the solvent to the compound comprising Formula (I) is from about 0.5:1 to about 10:1; the solvent is chosen from a protic solvent, an aprotic solvent, and combinations thereof; and the reaction is conducted at a temperature from about 10° to about 120° C.

15. The process of claim 6, wherein the optical activity of the compounds comprising Formulas (I) and (II) is (−) or (+), and the configuration of C-5, C-13, C-14, and C-9, respectively, is chosen from RRRR, RRSR, RRRS, RRSS, RSRR, RSSR, RSRS, RSSS, SRRR, SRSR, SRRS, SRSS, SSRR, SSSR, SSRS, and SSSS, provided that the C-15 and the C-16 carbons are both either on the alpha face of the molecule or the beta face of the molecule.

16. The process of claim 8, wherein the bis(allyl)-ruthenium(IV) complex catalyst is a bis-$\eta^3$-bonded ruthenium complex chosen from $\{Ru(\eta^3:\eta^3\text{-}C_{10}H_{16})(\mu\text{-}Cl)Cl\}_2$, $Ru(\eta^3:\eta^2:\eta^3\text{-}C_{12}H_{18})Cl_2$, and $\{Ru(\eta^3:\eta^3\text{-}C_{12}H_{20})(\mu\text{-}Cl)Cl\}_2$; the weight:weight ratio of the compound comprising Formula (I) to the bis-$\eta^3$-bonded ruthenium complex is from about 1:0.005 to about 1:0.02; the proton donor has a pKa of less than 5; the mole:mole ratio of the compound comprising Formula (I) to the proton donor is from about 1:1 to about 1:2; the reaction is conducted in the presence of a protic solvent; and the reaction is conducted at a temperature from about 65° to about 100° C.

17. The process of claim 16, wherein the optical activity of the compounds comprising Formulas (I) and (II) is (−), and the configuration of C-5, C-13, C-14, and C-9, respectively, is RSRR.

18. The process of claim 16, wherein the optical activity of the compounds comprising Formula (I) and (II) is (+), and the configuration of C-5, C-13, C-14, and C-9, respectively, is SRSS.

19. The process of claim 6, wherein the compound of Formula (II) is a pharmaceutically acceptable salt chosen from hydrochloride, sulfate, and bitartrate.

* * * * *